(12) United States Patent
Wästlund-Karlsson et al.

(10) Patent No.: US 8,748,690 B2
(45) Date of Patent: Jun. 10, 2014

(54) ABSORBENT ARTICLES COMPRISING ACIDIC CELLULOSIC FIBERS AND AN ORGANIC ZINC SALT

(75) Inventors: Jan Wästlund-Karlsson, Mölndal (SE); Jan Petrusson, Göteborg (SE); Madeleine Pehrson, Mölnlycke (SE); Åsa Lindström, Göteborg (SE); Linus Fredlinger, Kungsbacka (SE)

(73) Assignee: SCA Hygiene Products AB, Göteborg (SE)

( * ) Notice: Subject to any disclaimer, the term of this patent is extended or adjusted under 35 U.S.C. 154(b) by 375 days.

(21) Appl. No.: 12/514,942

(22) PCT Filed: Nov. 17, 2006

(86) PCT No.: PCT/EP2006/011066
§ 371 (c)(1), (2), (4) Date: May 14, 2009

(87) PCT Pub. No.: WO2008/058563
PCT Pub. Date: May 22, 2008

(65) Prior Publication Data
US 2011/0015596 A1 Jan. 20, 2011

(51) Int. Cl.
*A61F 13/15* (2006.01)

(52) U.S. Cl.
USPC .......................................... 604/359; 604/367

(58) Field of Classification Search
USPC ........... 604/359, 367, 368, 374, 375; 442/86; 424/65, 67, 608, 614, 617
See application file for complete search history.

(56) References Cited

U.S. PATENT DOCUMENTS

| | | | |
|---|---|---|---|
| 2,693,439 A | | 11/1954 | Blanchard et al. |
| 4,430,381 A | * | 2/1984 | Harvey et al. .................. 442/86 |
| 4,959,060 A | | 9/1990 | Shimomura et al. |
| 5,558,655 A | | 9/1996 | Jezzi et al. |
| 5,721,295 A | | 2/1998 | Bruggemann et al. |
| 5,847,031 A | | 12/1998 | Klimmek et al. |
| 5,882,638 A | | 3/1999 | Dodd et al. |
| 6,015,547 A | | 1/2000 | Yam |
| 6,153,209 A | | 11/2000 | Vega et al. |
| 6,217,890 B1 | | 4/2001 | Paul et al. |
| 6,417,425 B1 | | 7/2002 | Whitmore et al. |
| 6,462,252 B1 | | 10/2002 | Runeman et al. |
| 6,492,574 B1 | | 12/2002 | Chen et al. |
| 6,503,526 B1 | | 1/2003 | Krzysik et al. |
| 6,852,904 B2 | * | 2/2005 | Sun et al. ...................... 604/359 |
| 6,967,025 B2 | | 11/2005 | Di Cintio et al. |
| 7,005,557 B2 | | 2/2006 | Klofta et al. |
| 7,265,257 B2 | | 9/2007 | Baldwin et al. |
| 7,687,450 B2 | | 3/2010 | Li et al. |
| 2002/0128621 A1 | | 9/2002 | Kruchoski et al. |
| 2003/0077307 A1 | | 4/2003 | Klofta et al. |
| 2003/0135172 A1 | | 7/2003 | Whitmore et al. |
| 2003/0144637 A1 | | 7/2003 | Sun et al. |
| 2004/0014226 A1 | | 1/2004 | Schrof et al. |
| 2004/0024374 A1 | | 2/2004 | Hjorth et al. |
| 2004/0180093 A1 | | 9/2004 | Burton et al. |
| 2004/0213892 A1 | | 10/2004 | Jonas et al. |
| 2004/0227008 A1 | | 11/2004 | Runeman |
| 2005/0005869 A1 | * | 1/2005 | Fritter et al. .................. 119/173 |
| 2005/0101927 A1 | | 5/2005 | Joseph et al. |
| 2006/0036222 A1 | | 2/2006 | Cohen et al. |
| 2006/0036223 A1 | | 2/2006 | Baldwin et al. |
| 2006/0064068 A1 | | 3/2006 | Klofta et al. |
| 2006/0122569 A1 | | 6/2006 | Drevik et al. |
| 2009/0124989 A1 | | 5/2009 | Wastlund-Karlsson et al. |
| 2010/0047303 A1 | | 2/2010 | Yhlen et al. |
| 2011/0054430 A1 | | 3/2011 | Wastlund-Karlsson et al. |

FOREIGN PATENT DOCUMENTS

| | | |
|---|---|---|
| DE | 1792074 A1 | 10/1971 |
| DE | 2548344 A1 | 11/1976 |
| DE | 29 00 263 A1 | 7/1980 |
| DE | 38 08 114 A1 | 9/1989 |
| DE | 199 29 106 A1 | 12/2000 |
| DE | 200 15 738 U1 | 1/2001 |
| DE | 199 37 871 A1 | 2/2001 |
| DE | 102 56 569 A1 | 4/2003 |
| EP | 0 165 074 A2 | 12/1985 |
| EP | 0 311 344 A2 | 10/1988 |
| EP | 0 366 869 A2 | 5/1990 |
| EP | 0 564 307 A1 | 10/1993 |
| EP | 0 631 768 A1 | 1/1995 |

(Continued)

OTHER PUBLICATIONS

Wastlund-Karlsson et al., U.S. Appl. No. 12/084,880, "Absorbent Articles Comprising Acidic Superabsorber and an Organic Zinc Salt", filed May 12, 2008.

Yhlen et al., U.S. Appl. No. 12/514,911, "Absorbent Articles Comprising an Organic Zinc Salt and an Anti-Bacterial Agent or Alkali Metal Chloride or Alkaline Earth Metal Chloride", filed May 14, 2009.

Wastlund-Karlssson, U.S. Appl. No. 12/514,954, "Absorbent Articles Comprising a Peroxy Compound and an Organic Zinc Salt", filed May 14, 2009.

International Search Report issued on Apr. 13, 2007 in International Patent Application No. PCT/EP2006/011073 in related U.S. Appl. No. 12/084,880.

(Continued)

*Primary Examiner* — Melanie Hand

(74) *Attorney, Agent, or Firm* — Buchanan Ingersoll & Rooney P.C.

(57) ABSTRACT

An absorbent article, such as a diaper, panty diaper, sanitary napkin or incontinence device includes a liquid-permeable topsheet, a backsheet and an absorbent core enclosed between the liquid-permeable topsheet and the backsheet. The absorbent core includes acidic fluff pulp having a pH of 5.5 or less and an organic zinc salt, in particular zinc ricinoleate. The combination of organic zinc salt and acidic fluff pulp exerts a synergetic effect in the suppression of ammonia.

23 Claims, No Drawings

(56) References Cited

FOREIGN PATENT DOCUMENTS

| | | |
|---|---|---|
| EP | 0 640 330 A1 | 3/1995 |
| EP | 0 878 481 A1 | 11/1998 |
| EP | 1 034 804 A1 | 9/2000 |
| EP | 1 217 978 A1 | 7/2002 |
| EP | 1 532 990 A1 | 5/2005 |
| GB | 1 282 889 | 7/1972 |
| GB | 1 477 571 | 6/1977 |
| GB | 2 084 872 | 4/1982 |
| GB | 2 326 348 A | 12/1998 |
| JP | 62-235364 A | 10/1987 |
| JP | 2-1265 A | 1/1990 |
| JP | 10-328284 A | 12/1998 |
| JP | 11-263850 A | 9/1999 |
| JP | 2000-505692 A | 5/2000 |
| JP | 2002-508222 | 3/2002 |
| JP | 2002-511005 A | 4/2002 |
| JP | 2003-510165 A | 3/2003 |
| JP | 2003-520105 A | 7/2003 |
| JP | 2003-521267 A | 7/2003 |
| JP | 2003-230623 A | 8/2003 |
| JP | 2004-285202 A | 10/2004 |
| JP | 2005-528971 A | 9/2005 |
| JP | 2009-515622 A | 4/2009 |
| JP | 2010-509953 A | 4/2009 |
| SE | 9502588 A | 1/1997 |
| SE | 9801951 A | 9/1999 |
| SE | 9804390 A | 6/2000 |
| WO | WO 92/13577 A1 | 8/1992 |
| WO | WO 95/01147 A1 | 1/1995 |
| WO | WO 97/02846 A1 | 1/1997 |
| WO | WO 97/45013 A1 | 12/1997 |
| WO | WO 97/46188 A1 | 12/1997 |
| WO | WO 97/46190 A1 | 12/1997 |
| WO | WO 97/46192 A1 | 12/1997 |
| WO | WO 97/46193 A1 | 12/1997 |
| WO | WO 97/46195 A1 | 12/1997 |
| WO | WO 97/46196 A1 | 12/1997 |
| WO | WO 98/17239 A1 | 4/1998 |
| WO | WO 98/26808 A2 | 6/1998 |
| WO | WO 98/57677 A1 | 12/1998 |
| WO | WO 99/00090 A1 | 1/1999 |
| WO | WO 99/17813 A1 | 4/1999 |
| WO | WO 99/30753 A1 | 6/1999 |
| WO | WO 99/45099 A1 | 9/1999 |
| WO | WO 00/00110 A1 | 1/2000 |
| WO | WO 00/10500 A1 | 3/2000 |
| WO | WO 00/35502 A1 | 6/2000 |
| WO | WO 00/35503 A1 | 6/2000 |
| WO | WO 00/35505 A1 | 6/2000 |
| WO | WO 00/69481 A1 | 11/2000 |
| WO | WO 01/15649 A1 | 3/2001 |
| WO | WO 01/24756 A1 | 4/2001 |
| WO | WO 03/051250 | 6/2003 |
| WO | WO 03/051410 A1 | 6/2003 |
| WO | WO 03/092568 A1 | 11/2003 |
| WO | WO 03/105916 A1 | 12/2003 |
| WO | WO 2005/035013 A1 | 4/2005 |
| WO | WO 2005/063310 A1 | 7/2005 |
| WO | WO 2005/081811 A2 | 9/2005 |
| WO | WO 2007/057043 A1 | 5/2007 |
| WO | WO 2007/057211 A1 | 5/2007 |
| WO | WO 2007/120617 A2 | 10/2007 |

OTHER PUBLICATIONS

Zekorn, R., "Zinc Ricinoleate," Cosmetics & Toiletries, Wheaton, IL vol. 112, 1997, pp. 37-40.

Böhmer et al., "Development and Analytic of Odor Absorber," Tenside, Surfactants, Detergents; Carl Hanser Verlag, Munchen DE, vol. 41, No. 6, 2004, pp. 282-286.

Official Action dated Feb. 28, 2011, issued in Chinese Patent Application No. 200680051348.7, and English language translation thereof.

Office Action issued on Mar. 9, 2011, in copending U.S. Appl. No. 12/084,880.

English language translation of an Official Action issued on Aug. 30, 2011 by the Japanese Patent Office in corresponding Japanese Patent Application No. 2009-536609.

International Preliminary Report on Patentability and Written Opinion issued in International Patent Application No. PCT/EP2006/011073, May 20, 2008, The International Bureau of WIPO, Geneva, CH (6 pages).

Official Action dated Sep. 15, 2010 issued in Russian Application No. 2009123021 (3 pages), and English-language translation thereof (3 pages).

Notice of Opposition filed May 19, 2011 in EP Application No. 2083873 (11 pages).

Official Action issued Aug. 30, 2011 by the Japanese Patent Office in JP Patent Application No. 2008-540525 (2 pages), and English Language translation (3 pages) thereof.

Official Action issued on Jul. 22, 2011 in U.S. Appl. No. 12/514,954 (8 pages).

Official Action issued on Oct. 28, 2011 in U.S. Appl. No. 12/514,954 (14 pages).

English language translation of Office Action issued Dec. 6, 2011 by the Japanese Patent Office in JP Patent Application No. 2009-536610 A (4 pages).

Office Action dated May 15, 2012 issued by the Japanese Patent Office in JP 2009-536609 (2 pages), and English-language translation thereof (3 pages).

Notice of Allowance dated May 15, 2012 issued by the Japanese Patent Office in JP 2008-540525 (4 pages).

Official Action issued by the U.S. Patent and Trademark Office in corresponding U.S. Appl. No. 12/084,880, Jun. 28, 2011, 11 pages.

Official Action issued by the U.S. Patent and Trademark Office in corresponding U.S. Appl. No. 12/514,954, Feb. 16, 2012, 13 pages.

Official Action issued by the U.S. Patent and Trademark Office in corresponding U.S. Appl. No. 12/514,911, Oct. 27, 2011, 15 pages.

Official Action issued by the U.S. Patent and Trademark Office in corresponding U.S. Appl. No. 12/514,911, Mar. 22, 2012, 11 pages.

Official Action issued by the U.S. Patent and Trademark Office in corresponding U.S. Appl. No. 12/514,911, Oct. 11, 2012, 16 pages.

Official Action (Advisory Action) issued by the U.S. Patent and Trademark Office in corresponding U.S. Appl. No. 12/514,911, Feb. 6, 2013, 2 pages.

* cited by examiner

ABSORBENT ARTICLES COMPRISING ACIDIC CELLULOSIC FIBERS AND AN ORGANIC ZINC SALT

The present invention relates to an absorbent article such as a diaper, panty diaper, sanitary napkin or incontinence device, which comprises an effective odour control system, and odour-controlling cellulosic fibers which can be used in such absorbent articles. The present invention relates in particular to such absorbent articles wherein acidic cellulosic fibers, such as acidic fluff pulp having a pH 5.5 or less, and an organic zinc salt such a zinc ricinoleate interact favorably, in particular synergetically to reduce malodours such as ammonia.

TECHNICAL BACKGROUND

One important area of development in the area of absorbent articles of the above-mentioned type is the control of odourous compounds forming typically after the release of body fluids, especially over a longer period of time. These compounds include fatty acids, ammonia, amines, sulphur-containing compounds and ketones and aldehydes. They are present as natural ingredients of body fluids or result from degradation processes of natural ingredients such as urea, which is broken down by microorganisms or bacteria occurring in the urogenital flora to ammonia.

Various approaches exist to suppress the formation of unpleasant odours in absorbent articles. WO 97/46188, WO 97/46190, WO 97/46192, WO 97/46193, WO 97/46195 and WO 97/46196 teach for instance the incorporation of odour inhibiting additives or deodorants such as zeolites and silica. The absorption of bodily liquids reduces however the odour inhibiting capacity of zeolites as soon as these become saturated with water, as mentioned for instance in WO 98/17239.

A second approach involves the addition of lactobacilli with the intention of inhibiting malodour-forming bacteria in the product. The incorporation of lactobacilli and their favourable effect are disclosed for instance in SE 9703669-3, SE 9502588-8, WO 92/13577, SE 9801951-6 and SE 9804390-4.

Moreover, it is known from WO 98/57677, WO 00/35503 and WO 00/35505 that partially neutralized superabsorbent materials (acidic superabsorbent materials) counteract the formation of unpleasant odours in absorbent articles. However, acidic superabsorbent materials absorb lower amounts of body fluid compared to regular superabsorbent materials (in the following also referred to as superabsorbent polymer, SAP). The absorbent articles described in the above-mentioned WO 98/57677 may additionally contain fluffed cellulose pulp having a pH value below 7, preferably below 6.

Further, U.S. Pat. No. 6,852,904 describes cellulose fibers treated with acidic odor control agents and their use in absorbent products.

Various known odour control systems are however not effective enough or loose their effectiveness too quickly to be accepted by consumers of absorbent products.

Therefore, an ongoing demand exists in the art for effective odour-control systems in absorbent articles.

From other technical areas it is further known that organic zinc salts of unsaturated hydroxylated fatty acids such as zinc ricinoleate are deodorizing active ingredients (see for instance DE 1792074 A1, DE 2548344 A1 and DE 3808114 A1).

It is one technical object of the present invention to overcome deficiencies discussed above in connection with the prior art.

It is one further technical object to provide an absorbent article having an efficient odour control system.

It is one further technical object of the present invention to considerably reduce or eliminate ammonia formation in absorbent articles.

Further objects will become apparent from the following description of the invention.

BRIEF DESCRIPTION OF THE INVENTION

The present invention relates to an absorbent article, such as a diaper, panty diaper, panty liner, sanitary napkin or incontinence device comprising a liquid-permeable topsheet, a (preferably liquid-impermeable) backsheet and an absorbent core enclosed between said liquid-permeable topsheet and said backsheet, wherein said absorbent core comprises acidic cellulosic fibers, in particular acidic fluff pulp fibers, having a pH value of 5.5 or less, and an organic zinc salt, in particular the zinc salt of a monocarboxylic acid.

The present invention also relates to acidic cellulosic fibers having a pH of 5.5 or less characterized in that they comprise the zinc salt of a monocarboxylic acid and their use for odour control, especially in the aforementioned absorbent articles.

In the present specification, the acidic cellulosic fibers (CF) having a pH value of 5.5 or less are oftentimes simply referred to as "acidic cellulosic fibers (CF)" and acidic fluff pulp having a pH value of 5.5 or less as "acidic fluff pulp".

The present inventors have found that the acidic CF, in particular fluff pulp, and organic zinc salt, in particular the zinc salt of a monocarboxylic acid such as zinc ricinoleate, interact in the suppression of ammonia while preferably keeping the natural bacterial flora in the urogenital region, and they completed the present invention based on this finding.

Without wishing to be bound by theory, the mechanism underlying the odour reduction of the present invention is assumed to be as follows. It was found that the ammonia which produces the malodour in absorbent products, such as incontinence products is formed in the following way:

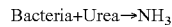

Bacteria+Urea→NH$_3$

In the present invention, the acidic CF, in particular fluff pulp fibers have the function of making the environment unfavourable for the bacteria while the organic zinc salt, e.g. the zinc ricinoleate removes the ammonia (NH$_3$) actually formed.

The aim of the present invention is to develop an absorbent article where the amount of unwanted bacteria or microorganisms, such as ammonia-producing bacteria does not increase during use.

DETAILED DESCRIPTION OF THE INVENTION

Throughout the specification and claims, the use of "comprising" is intended to cover also the more restricting meanings "essentially consisting of" and "consisting of".

As "absorbent article" we understand articles capable of absorbing body fluids such as urine, watery feces, female secretion or menstrual fluids. These absorbent articles include, but are not limited to diapers, panty diapers, panty liners, sanitary napkins or incontinence device (as used for instance for adults).

Such absorbent articles have a liquid-pervious topsheet, which during use is facing the wearer's body. They further comprise a (preferably liquid-impervious) backsheet, for instance a plastic film, a plastic-coated nonwoven or a hydrophobic nonwoven and an absorbent core enclosed between the liquid-pervious topsheet and the backsheet.

A suitable topsheet may be manufactured from a wide range of materials such as woven and nonwoven materials (e.g. a nonwoven web of fibers), polymeric materials such as apertured plastic films, e.g. apertured formed thermoplastic films and hydroformed thermoplastic films; porous foams; reticulated foams; reticulated thermoplastic films; and thermoplastic scrims. Suitable woven and nonwoven materials can be comprised of natural fibers (e.g. wood or cotton fibers), synthetic fibers (e.g. polymeric fibers such as polyesters, polypropylene or polyethylene fibers) or from a combination of natural and synthetic fibers. When the topsheet comprises a nonwoven web, the web may be manufactured by a wide number of known techniques. For example, the web may be spun-bonded, carded, wet-laid, melt-blown, hydroentangled, combinations of the above or the like. In accordance with the invention, it is preferred to make use of apertured plastic films (e.g. thermoplastic films) or nonwoven materials based on synthetic fibers, e.g. those made from polyethylene or polypropylene homo- or copolymers and polymer compositions based thereon.

Optionally, at least one further layer exists between the absorbent core and the topsheet and may be made from hydrophobic and hydrophilic web or foam materials. As "web material" we understand coherent flat fiber-based structures of paper tissue, woven or nonwoven type. The nonwoven material may have the same features as described above for topsheets.

Specifically, the at least one further layer may contribute to fluid management, for instance in the form of at least one acquisition/distribution layer. Such structures are taught for instance by U.S. Pat. No. 5,558,655, EP 0 640 330 A1, EP 0 631 768 A1 or WO 95/01147.

"Foam materials" are also well known in the art and for instance described in EP 0 878 481 A1 or EP 1 217 978 A1 in the name of the present applicant.

The absorbent core, which may be partially or totally surrounded by a core wrap, comprises acidic cellulosic fibers, in particular acidic fluff pulp fibers, having a pH value of 5.5 or less.

The term "cellulosic fibers" also referred to as "CF" relates to fibers from wood, woody plants and certain non-woody plants and cellulose-based recycled and regenerated fibers. Woody plants include for instance deciduous (hardwood) and coniferous (softwood) trees. Non-woody plants include for instance cotton, flax, esparto, grass, milkweed, straw, jute hemp and bagasse. The cellulosic fibers are preferably "pulp fibers".

The term "pulp fibers" includes chemical pulp and mechanical pulp fibers.

According to DIN 6730, "chemical pulp" is a fibrous material obtained from plant raw materials from which most non-cellulose components have been removed by chemical pulping without substantial mechanical post-treatment. In case of chemical pulping processes such as the sulfite or sulfate (Kraft) process, primarily the lignin components and the hemi-cellulose components are dissolved from the wood to varying degrees depending on the field of application of the chemical pulp. The result is a fibrous material consisting primarily of cellulose.

"Mechanical pulp" is the general term for fibrous materials made of wood entirely or almost entirely by mechanical means, optionally at increased temperatures. Mechanical pulp is subdivided into the purely mechanical pulps (groundwood pulp and refiner mechanical pulp) as well as mechanical pulps subjected to chemical pretreatment: chemo-mechanical pulp (CMP), such as chemo-thermomechanical pulp (CTMP).

The starting pulps which may be used in the present invention may relate to primary fibrous materials (raw pulps) or to secondary fibrous materials, whereby a secondary fibrous material is defined as a fibrous raw material recovered from a recycling process. The primary fibrous materials may relate both to a chemically digested pulp and to mechanical pulp such as thermorefiner mechanical pulp (TMP), chemothermorefiner mechanical pulp (CTMP) or high temperature chemithermomechanical pulp (HTCTMP). Synthetic cellulose-containing fibers can also be used. Preference is nevertheless given to the use of pulp from plant material, particularly wood-forming plants. Fibers of softwood (usually originating from conifers), hardwood (usually originating from deciduous trees) or from cotton linters can be used for example. Fibers from esparto (alfa) grass, bagasse (cereal straw, rice straw, bamboo, hemp), kemp fibers, flax and other woody and cellulosic fiber sources can also be used as raw materials. The corresponding fiber source is chosen in accordance with the desired properties of the absorbent core, such as softness and absorption capacity in a manner known in the art. With regard to the softness of the products, the use of chemical raw pulps is also preferred, whereby it is possible to use completely bleached, partially bleached and unbleached fibers. The chemical raw pulps suitable according to the invention include, inter alia, sulfite pulps, kraft pulps (sulfate process), soda pulps (cooking with sodium hydroxide), pulps from high-pressure cooking with organic solvents (e.g. Organosolv, Organocell, Acetosolv, Alcell) and pulps from modified processes (e.g. ASAM, Stora or Sivola process). Among the kraft pulps, it is possible to use those which were obtained in continuous cooking systems (MCC (modified continuous cooking), EMCC (extended modified continuous cooking) and ITC (isothermal cooking)). The products of discontinuous kraft processes (e.g. RDH (rapid displacement heating), Superbatch and Enerbatch) are also suitable as a starting product. The sulfite processes include the acidic sulfite/bisulfite processes, bisulfite process, "neutral sulfite semi-chemical pulping" (NSSC) process and alkaline sulfite processes such as processes in which in addition to aqueous alkali, sulfite and/or anthraquinone in combination with organic solvents such as methanol were used for cooking, e.g. the so-called ASAM process (alkali sulfite anthraquinone methanol). The major difference between the acidic and neutral or alkaline sulfite processes is the higher degree of delignification in acidic cooking processes (lower kappa numbers). The NSSC process provides semi-chemical pulps which are advantageously defibered in downstream mechanical fibrillation before they are used according to the invention for the purpose of oxidation. The sulfite and kraft pulps considerably differ in terms of their fibrous material properties. The individual fiber strengths of sulfite pulps are usually much lower than those of kraft pulps. The mean pore width of the swollen fibers is also greater in sulfite pulps and the density of the cell wall is lower compared to sulfate pulps, which simultaneously means that the cell-wall volume is greater in sulfite pulps. For this reason, there are also obvious differences regarding water absorption and swelling behavior of the cellulosic fibrous materials, which must also be taken into consideration when selecting a material for the absorbent core.

For the purpose of the present invention, general cellulosic fibers, in particular pulp fibers as described above are also referred to as "standard CF" or "non-acidic CF".

The cellulosic fibers to be used in the absorbent core are preferably fluff pulp fibers. The term "fluff pulp fibers" as used herein is well known in the art of making paper and absorbent products. It refers to a variant of "standard CF" as described above which is characterized by its fluffy state which can be achieved by comminuting standard, chemical (e.g. Kraft or sulfite), mechanical (e.g. groundwood pulp and refiner mechanical pulp) or chemomechanical pulp (CMP), such as TMP, CTMP or HTCTMP. Preferably chemical or chemomechanical pulp, optionally in a bleached form is used for the preparation of fluff pulp. Fluff pulp may comprise mainly, preferably exclusively, softwood fibers which impart the necessary softness for use in absorbent products. Suitable wood pulp fibers for manufacturing fluff pulp are e.g. Southern Softwood Kraft and Northern Softwood Sulphite. There are various grades of fluff pulps, such as debonded, also called treated, fluff pulps which are softer than regular fluff. Main producers of fluff pulp are Weyerhaeuser Co. and Georgia Pacific Corp. in the U.S. and Finland-based Stora Enso Oy. For the purpose of the present invention, general fluff pulp as described above is also referred to as "standard fluff pulp" or "non-acidic fluff pulp". In the following, "fluff pulp" and "fluff CF" will be used as synonyma.

The pH value of standard CF, including standard fluff pulp varies significantly, e.g. depending on the production method. Generally, standard (fluff) CF have a pH of from above 5.5 to 6.5, preferably around 6. Unlike standard (fluff) CF, the acidic (fluff) CF for use in the present invention have a pH of 5.5 or less. For removing bacteria, a pH value of 5.0 or less is advantageous. The pH value of the acidic (fluff) CF is preferably 2.0 to 5.0, more preferably 2.5 to 4.5, still more preferably 3.0 to 4.0 and most preferably 3.2 to 3.6. The pH of CF can be measured using the standard test Tappi T 509-02, in particular Tappi method T 509 om-02.

The acidic (fluff) CF fibers may also be admixed with standard (fluff) CF and/or superabsorbent polymer material (SAP).

In the corresponding absorbent core and, if applicable, each layer thereof, the total amount of cellulosic fibers, i.e. acidic (fluff) CF or a mixture of acidic and non-acidic (fluff) CF, is preferably 90 to 30 wt.-%, more preferably 80 to 35 wt.-%, in particular 70 to 40 wt.-%, for instance 70 to 50 wt.-%, based on the weight of the entire mixture of (fluff) CF and superabsorbent materials (without organic zinc salt). The term "(fluff) CF" is used as abbreviation for "non-fluffed cellulosic fibers such as non-fluffed pulp and/or fluff cellulosic fibers, i.e. fluff pulp"

If used in admixture, the weight ratio of acidic (fluff) CF and non-acidic (fluff) CF is not particularly restricted (e.g. 5/95 to 95/5, 10/90 to 90/10, 20/80 to 80/20). Accordingly, weight ratios of acidic (fluff) CF/non-acidic (fluff) CF of 100/0 to 50/50 (e.g. 95/5 to 60/40, 90/10 to 70/30) can be preferably selected depending on the properties to be achieved.

As indicated above, the absorbent core may further comprise a superabsorbent material, which may be acidic or non-acidic. According to one embodiment, the absorbent core contains an acidic superabsorbent material having a pH value of 5.5 or less (measured according to EDANA WSP 200.2), and according to a second alternative embodiment, the absorbent core does not contain such a material.

The total amount of the superabsorbent material may be 10 to 70 weight %, based on the weight of the core (excluding the organic zinc salt).

The term "superabsorbent material" is well known in the art and designates water-swellable, water-insoluble materials capable of absorbing the multiple of their own weight in body fluids. Preferably, the superabsorbent material is capable of absorbing at least about 10 times its weight, preferably at least about 15 times its weight, in particular at least about 20 times its weight in an aqueous solution containing 0.9 wt.-% of sodium chloride (under usual measuring conditions where the superabsorbent surface is freely accessible to the liquid to be absorbed). To determine the absorption capacity of the superabsorbent material, the standard test EDANA WSP 241.2 can be used.

The acidic and non-acidic superabsorbent materials can be distinguished by way of their pH value. While non-acidic SAPs (also referred to as standard SAPs) have a pH which lies e.g. in a range of 5.8 or more, acidic SAPs have a pH of 5.5 or less. Consequently, non-acidic SAPs may increase the pH in the absorbent core comprising acidic (fluff) CF according to the invention. Therefore, when acidic (fluff) CF according to the invention are used along with non-acidic SAPs, the pH of the acidic (fluff) CF used is preferably low enough to achieve a pH of the absorbent core of 5.5 or less, preferably 5.0 or less, more preferably from 3.0 to 5.0 after wetting. The pH of the absorbent core is measured according to the test method A described in the examples. While the pH of the acidic (fluff) CF to achieve the above pH of the absorbent core depends on the relative amount of acidic fluff pulp and non-acidic SAP in the absorbent core, the acidic (fluff) CF preferably have a pH value of 2.5 to 4.5, preferably from 3.0 to 4.0 and most preferably from 3.2 to 3.6 in this case.

In addition to the above materials, i.e. acidic (fluff) CF and optionally non-acidic (fluff) CF and superabsorbent material, the absorbent core may comprise, in admixture, other absorbent materials. Any other absorbent material that is generally compressible, conformable, non-irritating to the wearer's skin and capable of absorbing and retaining liquids such as urine and other body exudates can be used. Examples of other absorbent materials to be incorporated in the absorbent core include a wide variety of liquid-absorbent materials commonly used in disposable diapers and other absorbent articles such as creped cellulose wadding; melt blown polymers, including co-form; chemically stiffened, modified or cross-linked cellulosic fibers; tissue, including tissue wraps and tissue laminates, absorbent foams, absorbent sponges, absorbent gelling materials, or any other known absorbent materials or combinations of materials.

As indicated before, the absorbent core in the absorbent article of the invention may also contain fibers others than acidic CF, such as acidic fluff pulp fibers. These other fibers are preferably also capable of absorbing body liquid as is the case for hydrophilic fibers. Most preferably the fibers are other cellulosic fibers such as standard fluff pulp, cotton, cotton linters, rayon, cellulose acetate and the like. The standard fluff pulp can be of the above-described mechanical or chemical type, the chemical pulp being preferred.

There are no specific restrictions as to the method of producing the acidic (fluff) cellulosic fibers for use in the present invention. According to a preferred embodiment, the acidic (fluff) CF are obtained by treating standard CF with an acidifying agent. If an acidifying agent is used the same differs structurally from the organic zinc salt.

The acidifying agents for use in the present invention are not specifically limited in kind, as long as they do not disintegrate or decompose the standard fluff pulp being treated. One example is $SO_2$-water. Preferably the acidifying agent is a suitable acid, e.g. a weak acid or a salt thereof. The use of halogen-free non-oxidizing acids is preferred. Suitable acids are those which when incorporated in the standard (fluff) CF will not release any substances which may be harmful or acrid to skin. It should be noted that the skin in the region which comes into contact with absorbent articles is very sensitive, in infants and adults, alike. Hence, the acid used as an acidifying agent is preferably one that is approved of or admitted for use in food and/or cosmetics.

Preferably the acidifying agent is selected from optionally hydroxyl-substituted mono- and polycarboxylic acids, their salts, and mixtures thereof. The mono- or polycarboxylic acid may be aliphatic or aromatic. The salt is preferably an alkali metal (e.g. K or Na) or earth alkaline metal salt (e.g. Ca or Mg). If used in salt form, the acidifying agent, preferably the optionally hydroxyl-substituted mono- and polycarboxylic acid is only partially neutralized to provide acidic solutions in water.

The optionally hydroxyl-substituted monocarboxylic acid is preferably selected from saturated or unsaturated, linear or branched aliphatic carboxylic acids which preferably have from 1 to 18 carbon atoms, more preferably 2 to 8 carbon atoms, in particular 2 to 4 carbon atoms. The acid may be substituted by one, two or more hydroxy groups. Examples of this monocarboxylic acid include formic acid, acetic acid or propionic acid or lactic acid.

The optionally hydroxyl-substituted polycarboxylicacid (e.g. diacid or triacid) may also be substituted by one, two or more hydroxy groups. The organic (poly)acid may be an unsaturated (e.g. mono- or diunsaturated) or saturated, linear or branched aliphatic carboxylic acid preferably having from 2 to 18 carbon atoms, more preferably 3 to 8 carbon atoms, e.g. 4 to 6 carbons atoms. Examples thereof include oxalic acid, malic acid, maleic acid, malonic acid, succinic acid, tartaric acid, citric acid or sorbic acid.

The use of optionally hydroxyl-substituted polyacids, their salts and mixtures thereof is preferred. These polyacids are preferably employed in a partially neutralized state and thus capable to act as buffer. The degree of neutralization preferably ranges from 15 to 95% of the carboxyl groups and is more preferably 30 to 90%, e.g. 50 to 80%. Such partially neutralized polycarboxylic acids can also be provided by mixing polyacid and the corresponding salt in the necessary molar ratio.

Generally it is preferred to select among the above mono- and polyacids weak acids, in particular those having a pK value of at least 1.5, more preferably at least 2, even more preferably at least 3, e.g. 4 to 5 (for polyacids the pK1 value) measured in water at 25° C.

Most preferably, the acidifying agent is selected from aqueous solutions of citric acid, oxalic acid, lactic acid, malic acid, malonic acid, maleic acid, succinic acid, tartaric acid, sorbic acid, formic acid, salts thereof, and mixtures thereof. The most preferred acidifying agent for use in the present invention is citric acid and its salts.

The acidic CF, in particular the acidic fluff CF can be obtained by treating standard (fluff) CF with a solution of the acidifying agent. The same is preferably used in a concentration of 0.5 to 10 weight-% and preferably furnishes a pH of about 2 to 6, in particular 3 to 5. Desirably, the concentration of acidifying agent is selected such that the weight ratio of acidifying agent(s) to dry CF is about 1 to 20%, in particular 3 to 10%. The solution used for the treatment is preferably aqueous although volatile organic solvents may also be used as this facilitates the drying of the (fluff) CF.

The treatment of the standard (fluff) CF with the solution of the acidifying agent is achieved by combining standard (fluff) CF with the solution of the acidifying agent (e.g. by preparing a slurry, dipping or spraying) followed by the preferred steps of mixing and/or drying the mixture, followed by an optional fiberization step to break apart possibly aggregated fibers. Said drying may be achieved by letting the treated fibers stand at ambient air or preferably by heating, for instance to 50 to 95° C. Suitable heating conditions are also disclosed in U.S. Pat. No. 6,852,904 (col. 5, lines 30 to 53). The treatment is preferably done by the pulp manufacturer since this obviates the additional step of treating standard fluff pulp by the manufacturer of the absorbent article.

As to suitable acidic (fluff) cellulosic fibers, reference can also be made to U.S. Pat. No. 6,852,904 B2.

Very low amounts of organic zinc salts cooperate already with acidic (fluff) CF in a very efficient odour control. A preferred lower weight limit of organic zinc salt (calculated as zinc) seems to be at least $10^{-5}$ g per g dry (fluff) CF. Herein the term "dry" used in relation to acidic (fluff) CF is to be understood such that no water has been added to the acidic SAP and that the only water present in the acidic (fluff) CF is the unavoidable residual water from manufacturing. For the purpose of the present application, an acidic (fluff) CF or an absorbent core is preferably regarded as "dry" after a circular test sample thereof having a thickness of 5 to 6 mm, a diameter of 5 cm and which has been compressed to a bulk of about 8-10 cm$^3$/g has been kept for at least one week at ambient temperature (e.g. 20° C.) and a specific relative humidity, e.g. 50% RH.

More preferably, the organic zinc salt is present in amounts of at least $5 \times 10^{-5}$ g, even more preferably at least $10^{-4}$ g, even more preferably at least $5 \times 10^{-4}$ g, even more preferably at least $10^{-3}$ g per g acidic (fluff) CF. There is no specific upper limit, even though for economic reasons, a point may be reached where it may no longer be useful to further increase the zinc content, for instance beyond values of 0.1 or 1 g zinc per g acidic (fluff) CF, if this is not accompanied by an enhanced odour suppression.

The amount of organic zinc salt in the absorbent core is also not specifically limited. However, the amount is preferably at least $1 \times 10^{-5}$, more preferably at least $1 \times 10^{-4}$, most preferably at least $5 \times 10^{-4}$ g Zn per g dry absorbent core.

There are also no specific restrictions regarding the organic zinc salt to be used. In accordance with one embodiment of the present invention, at least one zinc salt of an organic carboxylic acid, in particular monocarboxyllic acid, having preferably 2 to 30 carbon atoms, in particular 12 to 24 carbon atoms is used. The carboxylic acid group may be attached to aliphatic, aliphatic-aromatic, aromatic-aliphatic, alicyclic, or aromatic residues, wherein the aliphatic chain or the alicyclic ring(s) may be unsaturated and are optionally substituted, for instance by hydroxy or C1 to C4 alkyl. These salts include zinc acetate, zinc lactate, zinc ricinoleate and zinc abietate. More preferably, the zinc salt is the zinc salt of an unsaturated hydroxylated fatty acid having 8 to 18 carbon atoms. Although there is no specific restriction regarding the number of unsaturated double bonds or hydroxy groups, those fatty acids having one or two unsaturated double bonds and one or two hydroxyl groups seem to be preferred. The most preferred embodiment is zinc ricinoleate. According to one embodiment of the present invention, the organic zinc salt is activated by means of an amino acid as in TEGO® Sorb available from Degussa.

The organic zinc salt to be used in the present invention may also be capable of removing malodorous substances chemically based on amines, e.g., nicotine in cigarette smoke, thiocompounds, e.g., allicin in garlic and onions, and acids, e.g., isovaleric acid in human sweat, and butyric acid. For instance, zinc ricinoleate which is, e.g., marketed by Degussa under the tradename TEGO® Sorb has the described additional odor removing effect apart from removing ammonia.

The present invention is also not subject to any limitations regarding the technique of incorporating the organic zinc salt into the absorbent core. Dipping and spraying are preferred.

For instance, it is conceivable to treat the fibers [acidic (fluff) CF, optionally in admixture with non-acidic (fluff) CF] present in the absorbent core with a solution of the organic zinc salt prior to, during or after admixture with other absorbent materials such as SAP and prior to, during or after formation of the absorbent core from said absorbent materials.

According to one preferred embodiment, acidic (fluff) cellulosic fibers, optionally in admixture with non-acidic (fluff) CF are treated as such, i.e. in the absence of other absorbent materials, with a solution of the organic zinc salt.

Alternatively, standard (fluff) CF are treated simultaneously (e.g. by spraying, preparing a slurry, or dipping) with acidifying agent and organic zinc salt. Then, the above-mentioned, preferably aqueous solution containing the acidifying agent also includes the organic zinc salt, in particular the zinc salt of a monocarboxylic acid such as zinc ricinoleate as second component. The zinc salt is preferably contained in amounts leading to the above disclosed Zn contents per dry acidic CF. Regarding other treatment conditions, reference can be made to the above description of manufacturing acidic (fluff) CF.

Both techniques can be equally carried out with the (fluff) CF fibers (for instance by preparing a slurry, spraying or dipping the fibers into said solution) and (fluff) CF sheets (e.g. by dipping or spraying) as prepared by the manufacturer prior to the delivery of the sheets to the manufacturer of the absorbent articles. These two techniques are especially preferred since they avoid the extra step of spraying the organic zinc salt solution when manufacturing the absorbent article. The other optionally present absorbent materials such as SAP are then added during or after formation of the absorbent core.

Preferably, the cellulosic fibers and/or the SAP are pretreated by adding a solution of the acidifying agent and organic zinc salt, and then these are incorporated into the absorbent core during core formation.

According to the above spraying techniques, the solution containing the organic zinc salt, in particular zinc ricinoleate can be sprayed on one or both sides of the absorbent core, or one of both sides of individual layers constituting the same.

The solvent used for the solution of organic zinc salt can be water, a preferably volatile organic solvent such as ethanol or a mixture of water and a water-miscible organic solvent such as ethanol. Preferably, the organic zinc solvent is present in the solution in a relatively high concentration, preferably 1 to 30 wt.-%. The use of such concentrated solutions ensures that the absorption capacity of the superabsorbent material is not impaired more than necessary. Commercially available solutions of organic zinc salts such as TEGO® Sorb A30 available from Degussa (content of actives 30 weight %, zinc ricinoleate activated by an amino acid) can also be employed.

The backsheet typically prevents the exudates absorbed by the absorbent layer and contained within the article from soiling other external articles that may contact the absorbent article, such as bed sheets and undergarments. In preferred embodiments, the backsheet is substantially impervious to liquids (e.g., urine) and comprises a laminate of a nonwoven and a thin plastic film such as a thermoplastic film having a thickness of about 0.012 mm to about 0.051 mm. Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the absorbent article while still preventing exudates from passing through the backsheet. Exemplary breathable materials may include materials such as woven webs, nonwoven webs, composite materials such as film-coated nonwoven webs, and microporous films. Since there is always a trade-off between breathability and liquid-impermeability it can be desired to provide backsheets showing a certain, relatively minor liquid-permeability but very high breathability values.

The above elements of an absorbent article can be assembled, optionally together with other typical elements of absorbent articles in a manner known in the art.

The present invention also relates to acidic cellulosic fibers having a pH of 5.5 or less characterized in that they comprise the zinc salt of a monocarboxylic acid. In this organic zinc salt the monocarboxylic acid preferably has the features stated above. Most preferably the zinc salt is zinc ricinoleate.

Similarly the above description of cellulosic fibers, in particular fluff pulp fibers and techniques for acidification is fully applicable to the claimed acidic cellulosic fibers. According to one embodiment, these are obtainable by treating cellulosic fibers with an acidifying agent (as described above) and the zinc salt of a monocarboxylic acid. According to another embodiment, the acidifying agent is present in an amount of 1 to 20 weight-% based on the dry weight of the untreated fibers.

The present invention also extends to the use of such acidic cellulosic fibers for odour control, preferably in those areas where bacterial control is an issue, including absorbent articles as claimed as well wipes, such as wipes for the feminine hygiene, baby wipes, medical wipes and wipes for cleaning bathroom equipment, e.g. toilets; bandages; underpads; absorbent drapes; underpants etc. Their use for odour-control in absorbent articles of the above-described type is preferred.

The following examples and comparative examples illustrate the present invention.

EXAMPLES

Test Methods

A) pH of Absorbent Core

The pH of the absorbent core can be measured very precisely with the following method involving the preparation of a test absorbent core and pH measurement using the same.
Method 1: Preparation of Absorbent Cores for Test Absorbent cores were punched out of an absorbent core produced in a pilot plant. A standard method of mat forming a core was used in the production of the core in the pilot plant. The absorbent core consisted of a homogenous mixture of acidic (fluffed) pulp and optionally superabsorbent material. The absorbent core was compressed to a bulk of about 8-10 cm$^3$/g. The size of the punched cores was 5 cm in diameter, the weight of the same about 1.2 g.
Method 2: Measurement of pH in an Absorbent Core An absorbent core having a diameter of approximately 50 mm was prepared according to Method 1. A predetermined amount of Test liquid 1 was added, 16 ml to all samples, whereafter the absorbent core was left to swell for 30 minutes. Thereafter, pH was measured on the liquid squeezed out of the samples using a surface electrode, Flat-bottomed, type Single Pore Flat, Hamilton. The results of three tests were averaged for the measurement.
Test Liquid 1 (Referred to in Method 2):

Synthetic urine containing the following substances: KCl, NaCl, $MgSO_4$, $KH_2PO_4$, $Na_2HPO_4$, $NH_2CONH_2$. The pH in this composition is 6.0±0.5.

The test liquid to be used is 16 ml synthetic urine (as defined above) for each core absorbent body.

Example 1

Circular test absorbent cores having a weight of about 1.16 g and a diameter of 5 cm were punched out of an absorbent core produced in a pilot plant. A standard method of mat forming a core was used in the production of the core in the pilot plant. The absorbent core consisted of a homogenous mixture of acidic fluff pulp and superabsorbent material. The fluff pulp used was 0.69 g Weyerhaeuser acidic fluff pulp and the superabsorbent material was 0.47 g of a superabsorber (SXM 9155, Degussa). The acidic fluff pulp is commercially available from Weyerhaeuser under the material description TR118 and manufactured by treating ECF Kraft pulp based on 100% US Southern pine wood with 4% citric acid and 1% citrate as an additive. It has a pH of 3.4±0.2. The pH of the acidic fluff pulp was measured in accordance with the standard Tappi T 509-02. More specifically, the above pH value is the 5 minutes pulp sheet pH based on Tappi method T 509 om-02. The absorbent core was compressed to a bulk of about 8-10 cm$^3$/g.

To the absorbent core 1.3 ml of a 0.5 wt.-% solution of zinc ricinoleate (available from Degussa under the tradename TEGO® Sorb A30, suitably diluted) was added by either dripping the solution onto the surface (on one side) or dipping one side of the core into the solution. The treated absorbent body was left standing at ambient air for one week. This procedure led to a concentration of $5.55 \times 10^{-4}$ g Zn per g dry absorbent core. Then, the absorbent body was allowed to absorb 16 ml synthetic urine according to Method 3 as described below and allowed to stand at room temperature.

6 h and 8 h after the absorption of synthetic urine the amount of ammonia developed was measured.

Five measurements were averaged as mean value. The results are shown in Table 1.

Method 3: Measurement of Ammonia Inhibition in Absorbent Cores

Absorbent cores were prepared in accordance with Method 1. Test liquid 2 was prepared. Bacteria suspension of *Proteus mirabilis* was cultivated in nutrient broth 30° C. overnight. The graft cultures were diluted and the bacterial count was determined. The final culture contained approximately $10^5$ organisms per ml of test liquid. The absorbent core was placed in a plastic jar and the Test liquid 2 was added to the absorbent core, whereafter the container was incubated at 35° C. 6 and 8 hours respectively, whereafter samples were taken from the containers using a hand pump and a so called Dräger-tube. The ammonia content was obtained as a colour change on a scale graded in ppm or volume percent.

Test Liquid 2:

Sterile synthetic urine to which has been added a growth medium for micro-organisms. The synthetic urine contains mono- and divalent cations and anions and urea and has been prepared in accordance with the information in Geigy, Scientific Tables, Vol 2, 8$^{th}$ ed. 1981 p. 53. The growth medium for the micro-organisms is based on information of Hook- and FSA-media for entero-bacteria. The pH in this mixture is 6.6.

Comparative Example 1

An absorbent core was formed in the same manner as in Example 1, with the sole exception that a treatment with a solution of zinc ricinoleate was not carried out.

Comparative Example 2

An absorbent body was formed in the same manner as in Example 1 with the difference that a 6 wt.-% solution of zinc ricinoleate was used and the acidic fluff pulp was replaced with a standard fluff pulp (NB 416 from Weyerhaeuser). This procedure led to an amount of $6.66 \times 10^{-3}$ g Zn per g dry absorbent core.

The results in terms of ammonia formation of Example 1 and Comparative Examples 1 and 2 are shown in the following Table 1.

TABLE 1

| | sample description | ammonia formation (ppm) 6 h | ammonia formation (ppm) 8 h |
|---|---|---|---|
| CEx 1 | Acidic fluff pulp[1] | 38 | 760 |
| CEx 2 | Zn$^2$ + non-acidic fluff pulp[3] | <19 | 270 |
| Ex 1 | Acidic fluff pulp[1] + Zn$^2$ | 1 | 16 |

[1]Acidic fluff pulp (Weyerhaeuser, pH 3.4)
[2]Zinc ricinoleate
[3]NB 416 (Weyerhaeuser)

The above experiments show that the combined use of an acidic fluff pulp and an organic zinc salt such as zinc ricinoleate suppresses the formation of ammonia to a very surprising extent. Considering the fact that a human can vaguely detect the smell of ammonium at a concentration of 150 ppm, the present invention ensures that during use of an absorbent article, no ammonia odour will be perceived by the wearer.

The invention claimed is:

1. Absorbent article comprising a liquid-permeable topsheet, a backsheet and an absorbent core enclosed between said liquid-permeable topsheet and said backsheet, wherein said absorbent core comprises acidic cellulosic fibers having a pH value of 5.5 or less, and an organic zinc salt of a monocarboxylic acid, and wherein the amount of organic zinc salt is at least $10^{-5}$ g Zn per g dry acidic cellulosic fibers.

2. Absorbent article according to claim 1, wherein said cellulosic fibers are fluff pulp fibers.

3. Absorbent article according to claim 1, wherein the acidic cellulosic fibers comprised in the absorbent core are obtained by acidifying cellulosic fibers with an acidifying agent.

4. Absorbent article comprising a liquid-permeable topsheet, a backsheet and an absorbent core enclosed between said liquid-permeable topsheet and said backsheet, wherein said absorbent core comprises acidic cellulosic fibers having a pH value of 5.5 or less, and an organic zinc salt of a monocarboxylic acid, wherein the acidic cellulosic fibers comprised in the absorbent core are obtained by acidifying cellulosic fibers with an acidifying agent, and wherein the acidifying agent is an organic acid having a pK value of at least 1.5 (measured in water at 25° C.).

5. Absorbent article according to claim 3, wherein the acidifying agent is selected from aqueous solutions of citric acid, oxalic acid, lactic acid, malic acid, malonic acid, maleic acid, succinic acid, tartaric acid, sorbic acid, formic acid, salts thereof, and mixtures thereof.

6. Absorbent article according to claim 1, wherein the acidic fluff pulp has a pH value of 5.0 or less.

7. Absorbent article according to claim 1, wherein the acidic fluff pulp has a pH value of 2.0 to 5.0.

8. Absorbent article according to claim 1, obtained by treating the absorbent core or the acidic cellulosic fibers contained therein with a solution of the organic zinc salt.

9. Absorbent article according to claim 1, wherein the organic zinc salt is selected from zinc salts of carboxylic acids having 2 to 30 carbon atoms.

10. Absorbent article according to claim 9, wherein the carboxylic acid represents an unsaturated hydroxylated fatty acid having 8 to 18 carbon atoms.

11. Absorbent article according to claim 9, wherein the zinc salt is zinc ricinoleate.

12. Absorbent article according to claim 1, wherein the backsheet is liquid-impermeable.

13. Acidic cellulosic fibers having a pH of 5.5 or less, comprising a zinc salt of a monocarboxylic acid, wherein the amount of organic zinc salt is at least $10^{-5}$ g Zn per g dry acidic cellulosic fibers.

14. Acidic cellulosic fibers according to claim 13, wherein said monocarboxylic acid represents an unsaturated hydroxylated fatty acid having 8 to 18 carbon atoms.

15. Acidic cellulosic fibers according to claim 13, wherein said organic zinc salt is zinc ricinoleate.

16. Acidic cellulosic fibers according to claim 13, obtained by treating cellulosic fibers with an acidifying agent and the zinc salt of a monocarboxylic acid.

17. Acidic cellulosic fibers having a pH of 5.5 or less, comprising a zinc salt of a monocarboxylic acid, the acidic cellulosic fibers being obtained by treating cellulosic fibers with an acidifying agent and the zinc salt of a monocarboxylic acid, wherein said acidifying agent is an organic acids having a pK value (water, 25° C.) of at least 1.5.

18. Acidic cellulosic fibers according to claim 17, wherein said acidifying agent is present in an amount of 1 to 20 wt. % based on the dry weight of the untreated fibers.

19. Acidic cellulosic fibers according to claim 13, wherein the cellulosic fibers are fluff pulp fibers.

20. A method for controlling odour comprising utilizing the acidic cellulosic fibers according to claim 13.

21. A method according to claim 20 comprising controlling odour in absorbent articles.

22. Absorbent article according to claim 1, wherein the absorbent article is a diaper, panty diaper, sanitary napkin or incontinence device.

23. Absorbent article according to claim 1, wherein the acidic fluff pulp has a pH value of 3.0 to 4.0.

* * * * *